(12) United States Patent
Donenfeld (10) Patent No.: US 11,123,506 B2
(45) Date of Patent: *Sep. 21, 2021

(54) CONNECTOR AND ALERTING DEVICE (71) Applicant: Roger F. Donenfeld, Los Angeles, CA (US)

(72) Inventor: Roger F. Donenfeld, Los Angeles, CA (US)

( * ) Notice: Subject to any disclaimer, the term of this patent is extended or adjusted under 35 U.S.C. 154(b) by 350 days.

This patent is subject to a terminal disclaimer.

(21) Appl. No.: 16/134,085

(22) Filed: Sep. 18, 2018

(65) Prior Publication Data
US 2019/0054264 A1 Feb. 21, 2019

Related U.S. Application Data (63) Continuation-in-part of application No. 14/460,644, filed on Aug. 15, 2014, now Pat. No. 9,764,105.

(51) Int. Cl.
A61M 16/00 (2006.01)
A61M 16/08 (2006.01)
(Continued)

(52) U.S. Cl.
CPC .... *A61M 16/0051* (2013.01); *A61M 16/0816* (2013.01); *A61M 16/0672* (2014.02); *A61M 2039/1005* (2013.01); *A61M 2202/0208* (2013.01); *A61M 2205/13* (2013.01); *A61M 2205/14* (2013.01); *A61M 2205/183* (2013.01); *A61M 2205/3368* (2013.01); *A61M 2205/3553* (2013.01); *A61M 2205/3561* (2013.01);
(Continued)

(58) Field of Classification Search
CPC . A61B 2017/00119; A61B 2017/00123; A61F 2007/006; A61F 7/0097; A61M 16/0051; A61M 16/0672; A61M 2039/1005; A61M 2205/13; A61M 2205/14; A61M 2205/18; A61M 2205/183; A61M 2205/581; A61M 2205/583; A61M 16/0816; A61M 16/0875; B01J 2219/00585; B01J 2219/0072; C07C 2102/10; C07D 209/14; C07D 209/82; C07D 401/04; C07D 401/14; C40B 40/00; F16J 15/0818; F16J 2015/085; F17D 5/005; G01M 3/26; G08B 21/12; G08B 21/14; G08B 3/02; G08B 3/06; G10K 5/00; Y10T 137/2262; Y10T 137/8326; F16L 37/084; F16L 37/0844

See application file for complete search history.

(56) References Cited

U.S. PATENT DOCUMENTS 9,764,105 B2 * 9/2017 Donenfeld ........ A61M 16/0875
10,099,025 B2 * 10/2018 Donenfeld ........ A61M 16/0051

* cited by examiner

Primary Examiner — Margaret M Luarca
(74) Attorney, Agent, or Firm — Samuel Alberstadt (57) ABSTRACT The present invention connects to tubing through which gas flows to a patient. An alert notifies monitoring personnel that oxygen flow to the patient has been interrupted, because the tubing has been disconnected. The invention comprises an adapter that is connected to a gas or oxygen source and a nipple over which the tubing fits and through which oxygen flows to the patient. When the tubing becomes disconnected from the nipple, the oxygen flow actuates an alert. The invention includes a fixed arm, a swing arm, and a spring. When the tubing becomes disconnected, the swing arm pivots and causes a switch actuator to engage a switch that sends a signal to an alert. The alert can be audible or visual.

18 Claims, 11 Drawing Sheets (51) Int. Cl.
*A61M 16/06* (2006.01)
*A61M 39/10* (2006.01)
(52) U.S. Cl.
CPC . *A61M 2205/3592* (2013.01); *A61M 2205/44* (2013.01); *A61M 2205/50* (2013.01); *A61M 2205/581* (2013.01); *A61M 2205/583* (2013.01); *A61M 2205/8206* (2013.01)

CONNECTOR AND ALERTING DEVICE

RELATED APPLICATIONS

This application is a continuation-in-part of application Ser. No. 14/997,618, which was filed Jan. 18, 2016, and issued as U.S. Pat. No. 10,099,025 on Oct. 16, 2018. The parent application is a continuation-in-part of U.S. Pat. No. 9,764,105, filed Aug. 15, 2014 as application Ser. No. 14/460,644, and issued Sep. 19, 2017.

FIELD OF THE INVENTION

The present invention is for use in systems that administer oxygen or other gases, such as a patient's oxygen found in hospital rooms, nursing homes, and even in-patient residences. Its purpose is to alert medical or other attendant personnel, or even the patient himself, that tubing has become disconnected from an oxygen source, and to indicate that a patient is no longer receiving oxygen.

BACKGROUND OF THE INVENTION

For patient care, a monitor or alerting device should be a critical component where oxygen tubing is used with a flow regulator and where a concern exists that the tubing can become disconnected, thus interrupting oxygen flow to the patient. Until now, such a device has not existed. This need for an alerting device can occur where tubing is connected to a gas supply through a flow regulator, and eventually to a nasal prong or face mask, such as in hospital rooms, nursing homes, outpatient and convalescent facilities, doctor's offices, diagnostic and procedure rooms, operating rooms, and private homes. In many situations, a barbed nipple, sometimes combined with a nut adapter (and also commonly referred to as a barbed nipple adapter or Christmas tree adapter), is attached to a flow regulator combined with a source of oxygen. Then, tubing runs from the barbed nipple to the patient's nasal cannula or facemask. Unfortunately, in these situations there is no warning device to alert medical personnel, or anyone looking after the patient, that the tubing has become disconnected from the barbed nipple and that a gas is flowing freely into the ambient air.

There are many potentially serious consequences of oxygen flowing through a barbed nipple adapter with the tubing disconnected. Most serious are the consequences of a patient not receiving oxygen. Medical personnel may not be aware of or alerted to that situation, believing a patient is receiving oxygen when in fact he is not. The same issue arises when a patient is responsible for administering and monitoring his own oxygen. Without an adequate supply of oxygen, the body's cells can stop functioning. Consequently, the patient can suffer hypoxia, stroke, brain damage, paralysis, poor wound healing, or other grave problems while medical personnel incorrectly believe the patient is receiving oxygen. This situation also wastes oxygen, an expensive and critical medical resource, and heightens the combustibility and flammability of the oxygen-enriched environment around the patient.

Safety and monitoring are becoming increasingly important in every aspect of clinical practice. Evidence is accumulating that clinical and hospital errors of all types are a far greater cause of morbidity and death than the medical profession has previously realized. Tracing individual outcomes back to their cause is not always possible, and even when it is, the medical profession is obligated to address both known and reasonably anticipated problems. Therefore, every aspect of clinical care must be scrutinized for safety, potentially deleterious effects, and the possibility of improvement. There has been a long-felt need to quickly identify when an oxygen tubing line has become disconnected from the oxygen source for the patient, because of its potentially fatal consequences. For decades, medical personnel have expressed their frustration with this problem. A solution would save medical resources and money, and, even more importantly, decrease preventable morbidity and mortality, i.e., prevent adverse unfavorable medical events and save lives.

SUMMARY OF THE INVENTION

The present invention solves the longstanding problem of the undetected disconnection of an oxygen tubing line. It is a safety device for alerting monitoring personnel that the tube providing oxygen to the patient has become disconnected. The invention improves upon the long-used barbed nipple, which previously has provided a connecting function without the safety of a disconnect warning, i.e., that nasal or mask tubing has been disconnected. The present invention detects the disconnection of tubing from the nipple and produces an alert that indicates the failure to deliver oxygen to the tube and ultimately the patient or some apparatus.

In one embodiment the invention comprises a fixed arm and a swing arm. The fixed arm includes a preferably barbed nipple that can be attached to gas tubing going to a patient, and an adapter to connect the nipple to the flow regulator or gas source. The flow regulator attachment mechanism may take a variety of forms, such as a screw-on or push-on type. The swing arm is attached to the fixed arm at the base with a hinge and is comprised of a spring and an alerting mechanism, such as a whistle or buzzer. The alert is actuated when tubing becomes disconnected from the nipple. The spring is releasably engageable with a stop or latch that is on the fixed arm. Preferably the spring is a leaf spring configured in a generally sinusoidal shape.

In another embodiment, the invention includes a fixed arm, an adapter for a nipple connectable to the tubing, another adapter for connecting the fixed arm to a source of gas, and an electrical compartment; a swing arm movably connected to the fixed arm and a spring urging the swing arm to move toward the fixed arm when tubing becomes disconnected; a switch disposed in the electrical compartment and actuatable when the swing arm moves toward the fixed arm when the tubing is disconnected; an electronic signal generator disposed in the electrical compartment and responsive to the switch being activated; and, an alert disposed in the electrical compartment and responsive to a signal from the electronic signal generator. The alert may be local or remote or both, and it may be sound or light or a combination of both.

BRIEF DESCRIPTION OF THE DRAWINGS

Below is a detailed description of the invention and its novel aspects and a variety of equivalents, and in that context refers to the following figures.

DETAILED DESCRIPTION OF THE INVENTION

Figure 1:
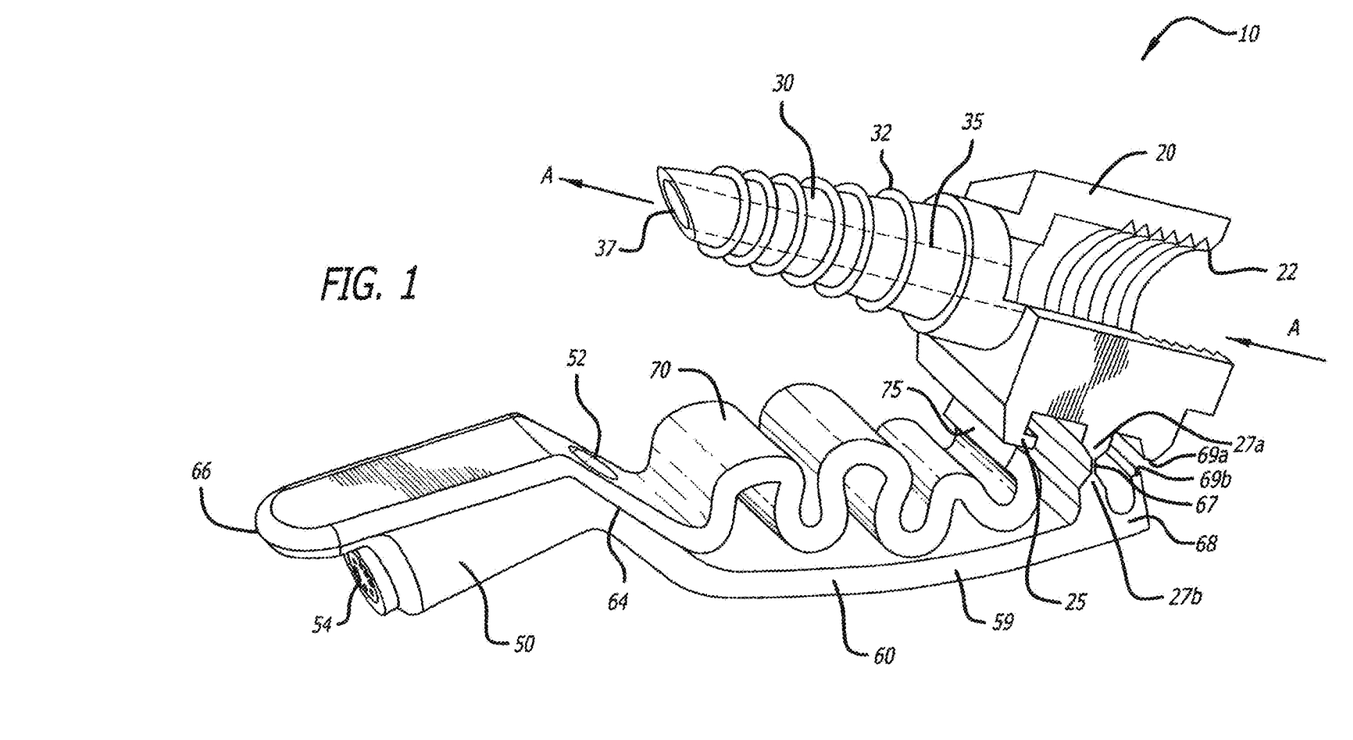
FIG. 1 is a perspective view of the invention before it is put to use.
Figure 2:
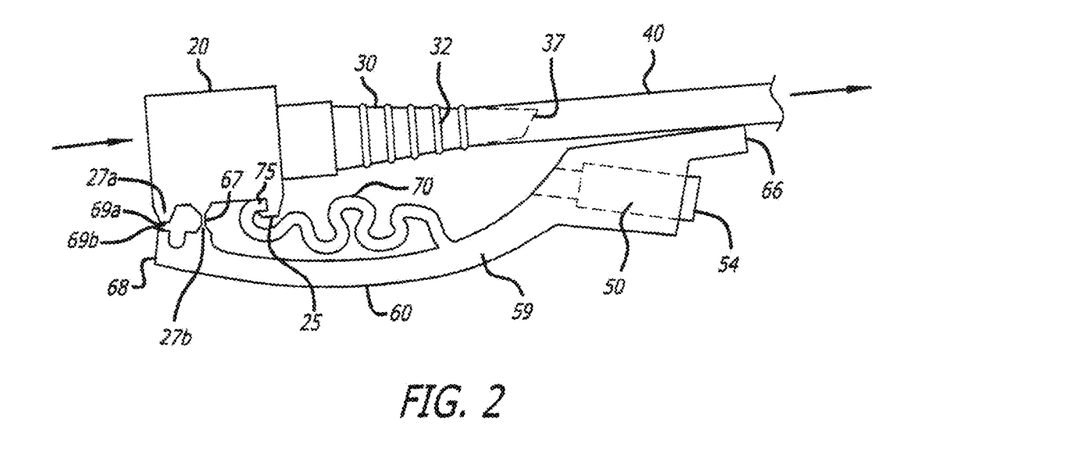
FIG. 2 is an elevation view of the invention while it is connected to a tube that delivers gas to the patient.
Figure 3:
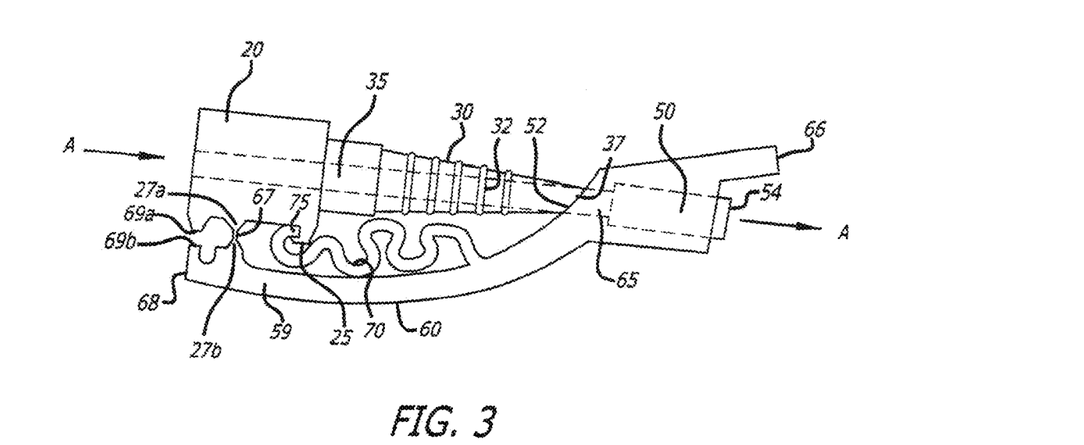
FIG. 3 is an elevation view of the invention when the tubing has been disconnected from the barbed nipple.

FIGS. 1-3 depict one embodiment of the invention 10. FIG. 1 shows the invention 10 before it is used; FIG. 2 shows it in use, with tube 40 connected to nipple 30, with oxygen flowing through the tube to the patient (not shown). Nipple 30 preferably though not necessarily includes barbs 32. FIG. 3 shows invention 10 in use when tube 40 has become disconnected from nipple 30, so that oxygen will pass through whistle 50 and alert personnel attending the patient. Gas, typically oxygen, flows in direction A, from the source of the gas toward the patient. In locations like a hospital room or nursing home, the nipple is typically connected to a flow regulator attached to a wall of the room (not shown). Oxygen is supplied, usually from a remote source, to the flow regulator, the nipple, and then tubing that connects to a patient's mask or nasal cannula. The source of the gas, the presence of gas flow regulators, and other such equipment are not part of the invention. In the embodiment depicted in FIGS. 1-3, a swing arm 59 pivots about hinge 67, which connects to base 60 that extends from one end 66 to the other end 68 of base 60. Spring 70 is attached to base 60 and curves around to spring end 75. The spring 70 has a somewhat irregularly shaped sinusoidal configuration, which increases the force the spring can hold. A fixed arm 20, which includes nipple 30 with barbs 32 and threaded nut adapter 22, is connected to the swing arm 59 by hinge 67, located between point 27a on the fixed arm 20 and point 27b on the swing arm 59. A stop comprised of surfaces 69a and 69b prevent hinge 67 from allowing too much relative movement of fixed arm 20 and swing arm 59 when the invention is not being used and is in an open, unlatched position as shown in FIG. 1. In the depicted embodiment, female threads of threaded nut adapter 22 are typically attached to a flow regulator or wall outlet having an adapter with male threads (not shown). Other threaded and non-threaded connections are also known in the art and can be used. Moreover, the invention should not be limited to a connection with wall outlets. It can be used wherever nipple adapters and similar such devices connect tubing to sources of gas with flow regulators, as is often seen on oxygen tanks. Similarly, the invention's connection to the source of the gas, such as by threaded nut adapter 22, is not restricted to threads as shown in FIG. 1. Flanges joined by screws, or snap-on, clip-on, push-on or other types of connections, may also be used. It goes without saying that the invention is not limited to use with oxygen, although that is the typical gas that is provided to the patient.

FIG. 2 depicts how the invention is set up while oxygen is flowing to the patient. Prior to using the invention, tube 40 is slid over nipple 30 with barbs 32. The friction created by the preferably conical frustum shape of nipple 30, together with barbs 32, secures the tube 40 in place. In a typical use of the invention, such as in a hospital room or nursing home, tube 40 can connect directly to a mask or nasal cannula (not shown) used by a patient. Tubing may also be connected to equipment. To engage the alerting function, threaded nut adapter 22 is threaded, snapped, or pushed on, or otherwise attached to a source of oxygen and a flow regulator. Then, pressure is applied to swing arm 59, which rotates around hinge 67 while fixed arm 20 with nipple 30 remains stationary. Continued application of force to swing arm 59 pushes the top of spring 70 down so spring end 75 moves toward fixed arm 20. Spring end 75 slides over latch 25 of fixed arm 20, so that the two are engaged. Once spring end 75 engages latch 25, spring 70 continues to urge swing arm 59 toward nipple 30, as seen in FIG. 2. Tube 40 must be stiff enough so that the force exerted by spring 70 does not squeeze or crimp the tubing, which would limit or block the flow of gas to the patient.

FIG. 3 depicts the invention when tube 40 has been accidentally disconnected from nipple 30, so that no oxygen is flowing to the patient. Spring end 75 remains engaged with latch 25, so that without the presence of tube 40, as shown in FIG. 2, swing arm 59 pivots so that surface 64 of base 60 engages end 37 of nipple 30. Interior flow path 35 of nipple 30 aligns with aperture 52 and flow path 65 of base 60. As a result, oxygen flowing through flow path 35 of nipple 30 passes through whistle 50, which is embedded in base 60. The whistle sounds as oxygen exits through aperture 54, alerting the personnel attending the patient.

The invention does not necessarily require that a separate whistle structure be embedded in base 60. An alternative to the embodiment depicted in FIGS. 1-3 is a unitary piece of thermoplastic in which an interior whistle chamber is created inside and as part of base 60. This result can be accomplished because embodiments like the one in FIGS. 1-3 can be manufactured by, for example, a 3D printer or a lost foam mold. Nevertheless, the invention should not be limited to such a unitary structure, and can be made of other materials, such as stainless steel, and can be manufactured using other methods. Likewise, as discussed below in relation to FIGS. 6-7, the alert mechanism need not be limited to a whistle.

Figure 4:
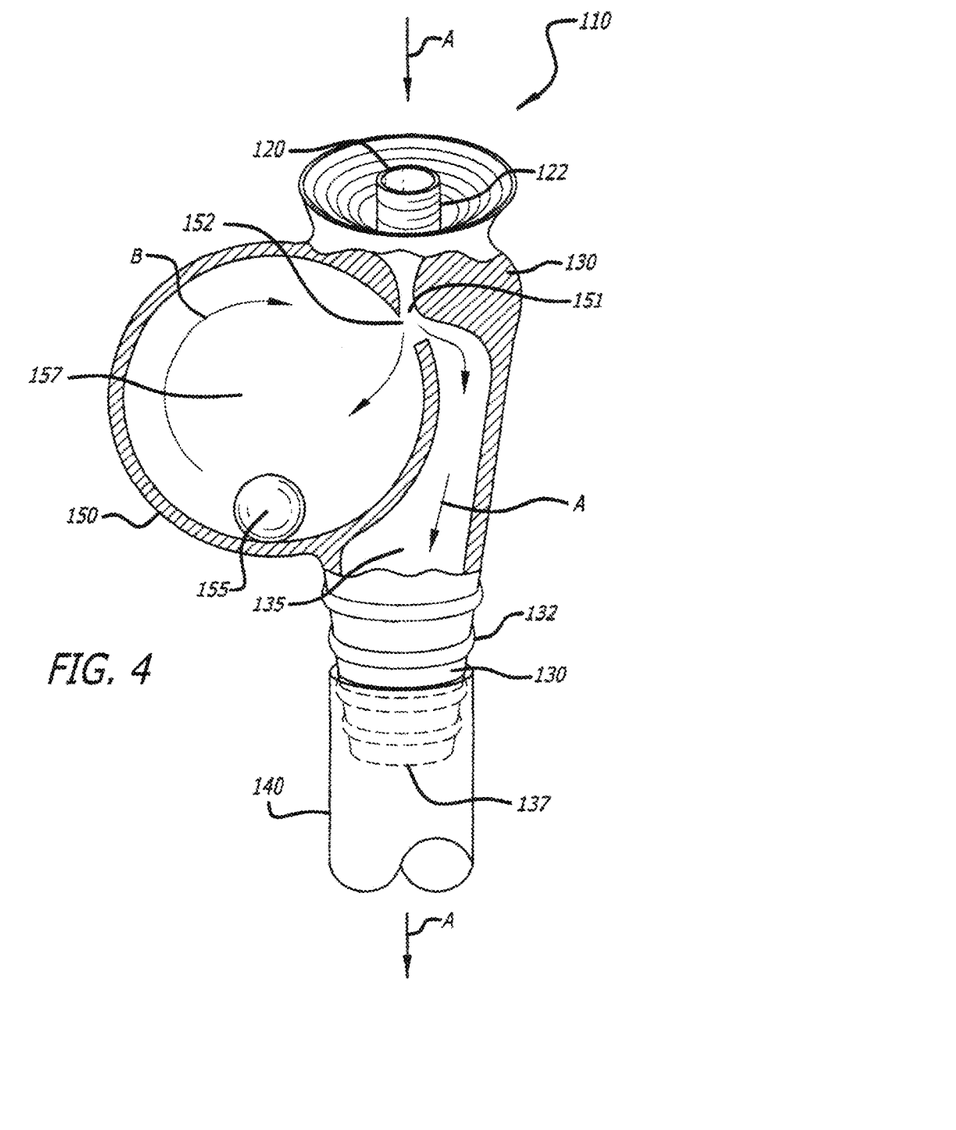
FIG. 4 is an elevation view of another embodiment of the invention.

FIG. 4 depicts another embodiment of the invention 110. A threaded adapter 120 is part of nipple 130 with barbs or ridges 132. Oxygen travels through flow path 135 the direction of arrow. Nipple 130 has a threaded adapter 120 with threads 122. One end of tube 140 connects to the end of nipple 130, so that oxygen can flow through tube 140 and to a mask or cannula on the patient's face (not shown). Whistle 150 is part of threaded adapter 120 and barbed nipple 130. When tube 140 is disconnected from nipple 130, the invention 110 functions somewhat like a whistle used by police or by referees of athletic contests. Oxygen flowing in the direction of arrow A divides at tip 151, causing a whistling sound. Some oxygen follows along flow path 135 and out the end 137 of nipple 130, while some oxygen passes through aperture 152 into chamber 157. The swirling oxygen B in chamber 157 moves ball 155 inside chamber 157, creating the distinctive whistle sound associated with a policeman's or referee's whistle.

In contrast, when tube 140 is connected to barbed nipple 130, no alerting sound is created. The oxygen moving along flow path 135 through barbed nipple 130 into tube 140 creates enough back pressure in chamber 157 of whistle 150 that chamber 157 tends to remain filled with oxygen. Thus, no flow can divide at edge 151 to create the whistle alert. Any sound that whistle 150 might create becomes muffled and attenuated as it moves through tube 140 toward the patient, so that it is imperceptible and does not create any false alarms.

Figure 5:
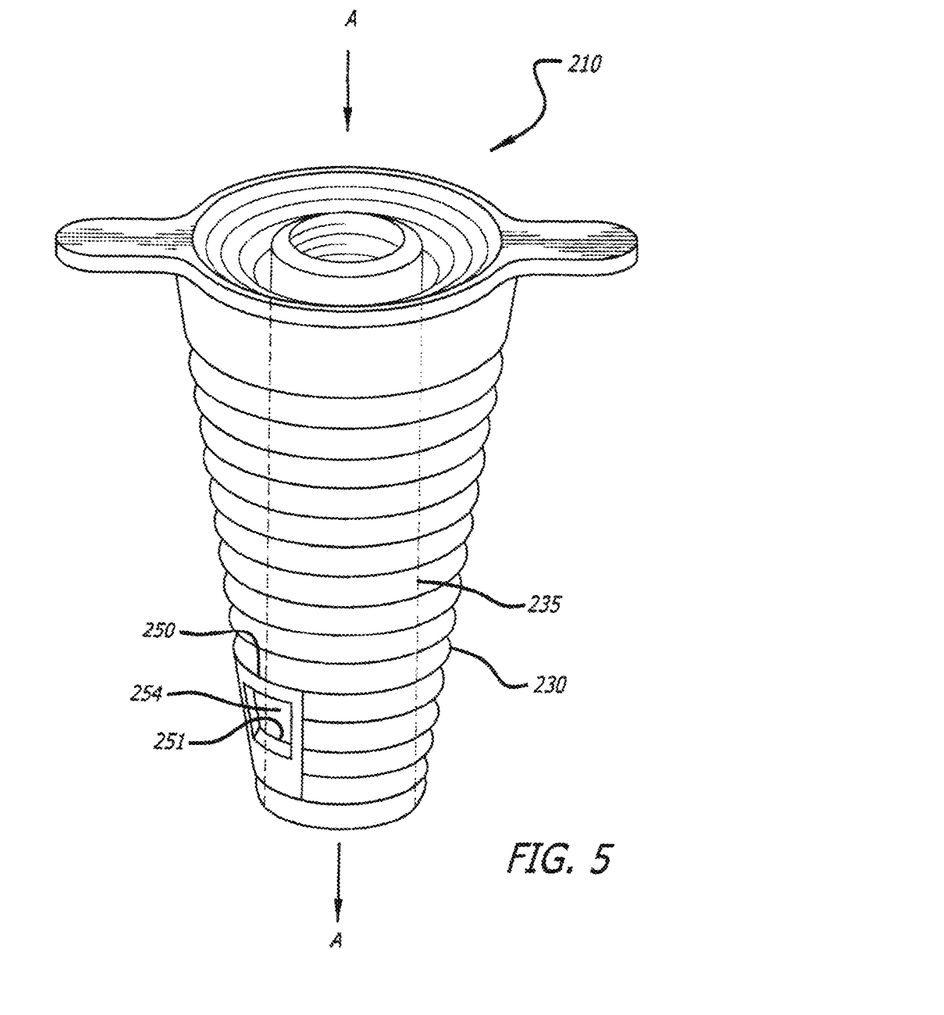
FIG. 5 is an elevation view of yet another embodiment of the invention.

FIG. 5 depicts yet another embodiment 210 of the present invention. In FIG. 5 the nipple 230 includes an aperture 254 that connects with the flow path 235. When a tube (not shown) is removed from the end of nipple 230, oxygen flowing over edge 251 creates a whistle sound. If the tube (not shown) covers aperture 254 of whistle 250, as it would when a patient is receiving oxygen, then oxygen cannot flow over edge 251 to create a whistle.

Figure 6:
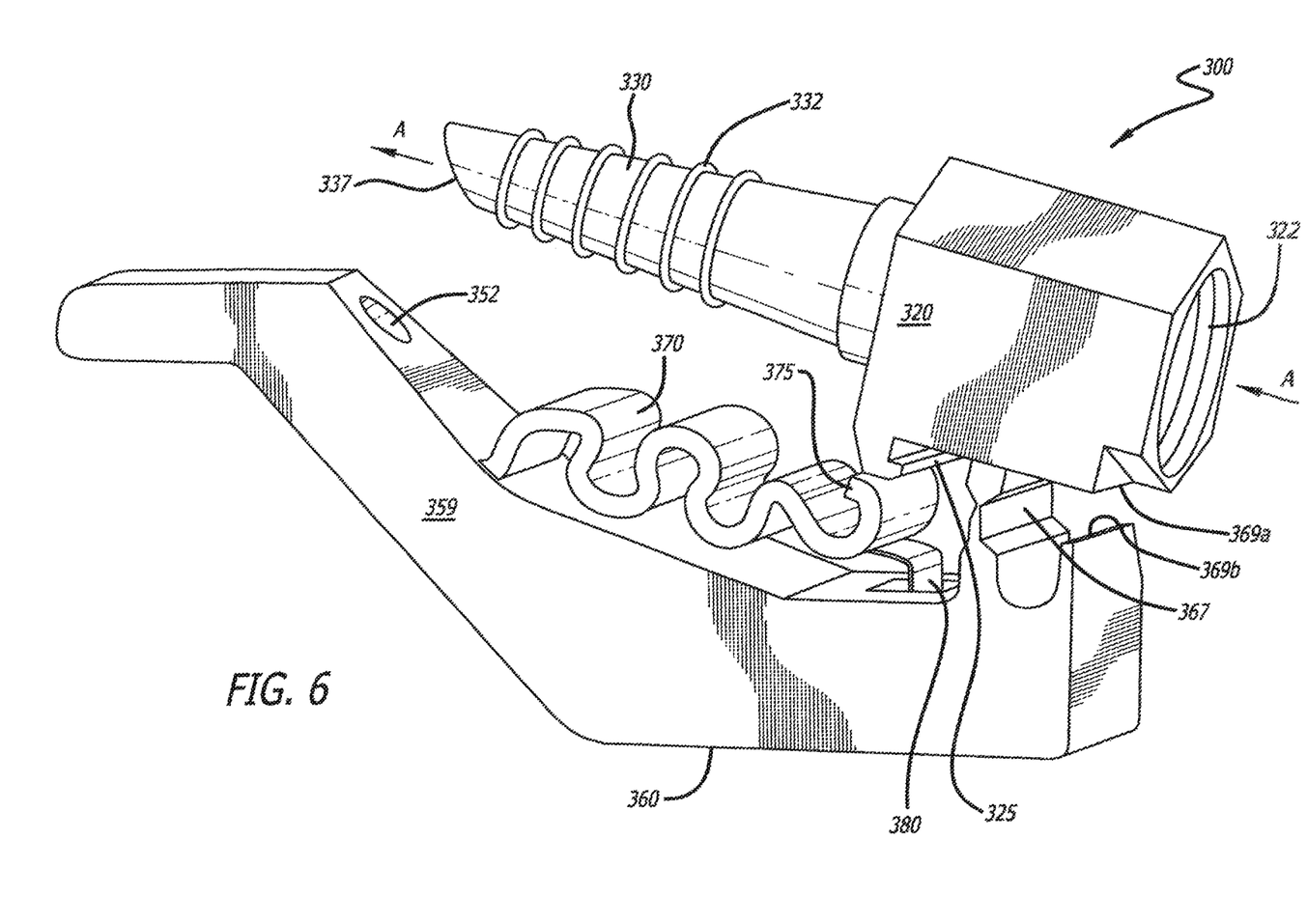
FIG. 6 is a perspective view of another embodiment of the invention.
Figure 7:
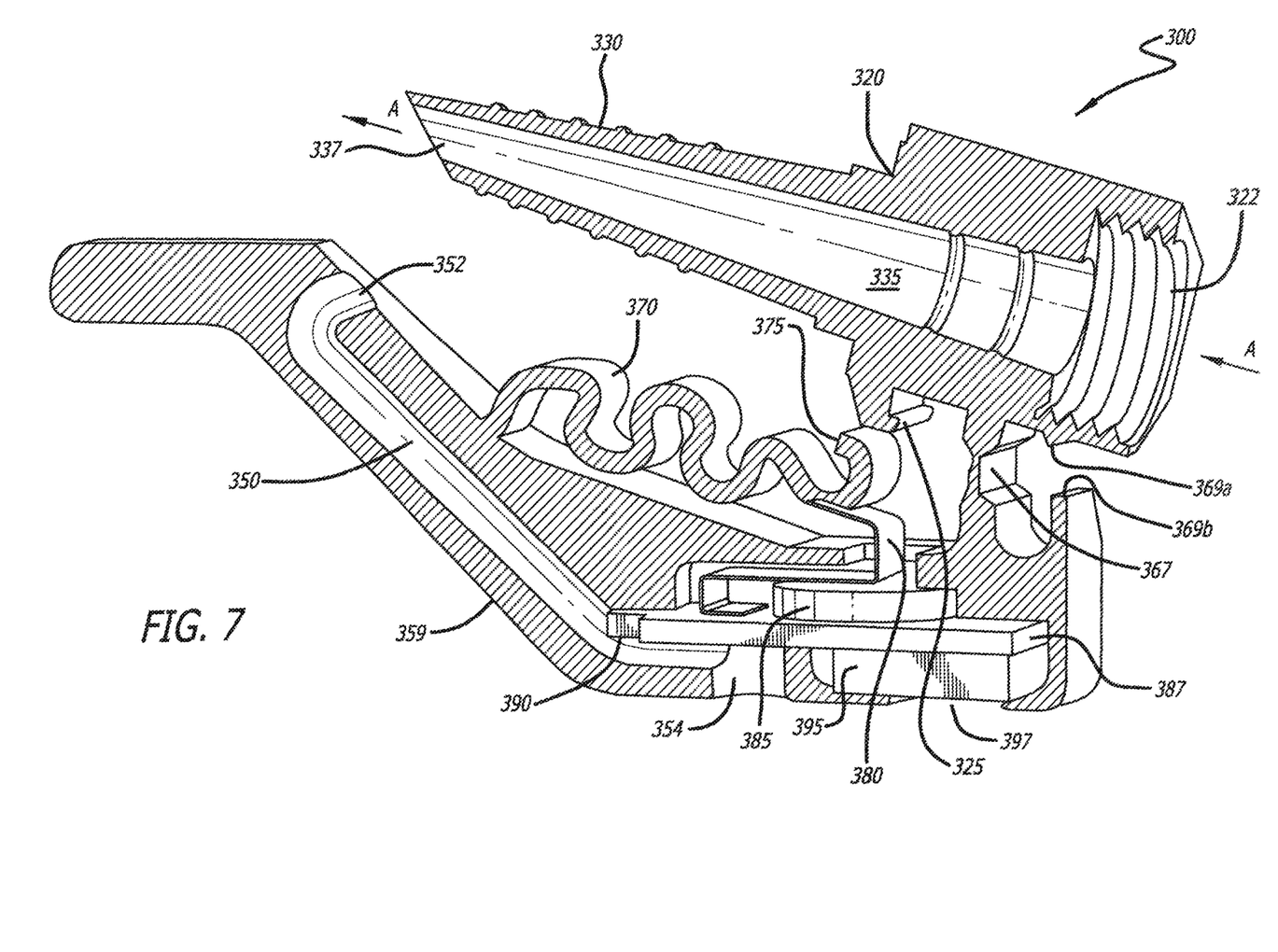
FIG. 7 is a section view through FIG. 6.

FIGS. 6-7 represent an embodiment of the invention that includes an electronic alert mechanism. As shown in FIG. 6, the exterior of this embodiment is quite similar in appearance and mechanical operation to the embodiment in FIGS. 1-3, with correspondingly similar numerals. The invention or connector 300 has a fixed arm 320 that includes nut adapter 322 and nipple 330 with barbs 332. Arrow A represents the flow direction that traverses flow path 335 exits through nipple end 337. Swing arm 359 includes base 360 and spring 370. Hinge 367 connects fixed arm 320 and swing arm 359, while stop surfaces 369a, 369b limit the relative rotation of the fixed and swing arms 320, 359 about hinge 367. Similar to FIG. 2, spring end 375 can engage latch 325, so that if tubing (not shown in FIGS. 6-7) were mounted on nipple 330, spring 370 would continue to urge swing arm 359 toward nipple 330. If tubing were disconnected from nipple 330 while spring end 375 and latch 325 were engaged, then nipple end 337 would align with aperture 352, so that gas would flow from fixed arm 320 into swing arm 359.

As shown in the FIG. 7 cross-section, the interior of swing arm 359 is different from the interior of swing arm 59 in FIGS. 1-3. In FIG. 7 the alert mechanism includes a switch 380, a battery 385 located on circuit board 387, microprocessor 390, and a noise generator such as buzzer 395. When tubing (not shown) is mounted on nipple 330 and spring end 375 and latch 325 are latched together, similar to the depiction of FIG. 2. Once latched, a slight force pulling swing arm 359 away from fixed arm 320 causes switch 380 to contact battery 385 and circuit board 387. A small current flows through circuit board 387 to microprocessor 390, which may include a resistor as a heating element, and a temperature sensor. As long as the tubing is connected, and there is a heat source, the thermistor senses no temperature cooling as would occur if gas tubing disconnects and gas were to flow through the swing arm and over circuit board 387 microprocessor 390. Thus, the alert mechanism perceives connector 300 as working properly, i.e., no alert is actuated when the tubing is connected to a patient or an apparatus. If swing arm 359 and fixed arm 320 close because tubing comes off the end of nipple 330, gas flows through nipple end 337, aperture 352, flow path 350, over the sensor in microprocessor 390, and out aperture 354. The flowing gas cools the sensor in microprocessor 390, which in turn causes buzzer 395 to sound or some other form of alert to actuate. Opening 397 permits the escape of the signal from buzzer 395, which could also be an alert such as a light. Subject to environmental and workplace regulations, and patient considerations, it is contemplated that the buzzer will generate a sound of 70-75 dB at 10 centimeters.

For cost and reliability, a simple configuration like the preceding description of the alert mechanism is preferred. Simpler configurations, however, also fall within the spirit of the invention. For example, a simple mechanical switch with electrical contacts (not shown) could replace the temperature sensing mechanism described in the preceding paragraph. If tubing were to come off nipple 330, so swing arm 359 would rotate toward fixed arm 320, one arm would physically contact the other arm in such a way as to activate a battery powered circuit that would send a signal to the alert mechanism. Those of skill in the art understand that such a switch could be configured in any of numerous ways at different locations on connector 300.

Furthermore, the electrically actuated alert presents the possibility of adding useful features. One useful feature would be a timing circuit that provides a delay—perhaps 10 or 15 seconds—before actuating the alert mechanism. This would prevent an unnecessary loud noise if someone had immediately perceived the disconnected tubing and had taken action. As another feature, the noise generator or buzzer 395 in connector 300 could be located remotely from connector 300, either elsewhere in the patient's room or even at a monitoring station remote from the room. The remotely located noise generator could be wirelessly linked to connector 300. In such cases the alerting mechanism need not even be a noise generator. For example, it could be a flashing light, a message appearing on a monitoring screen, or some combination of visual and sound alerts generated in one or more locations simultaneously.

Figure 8:
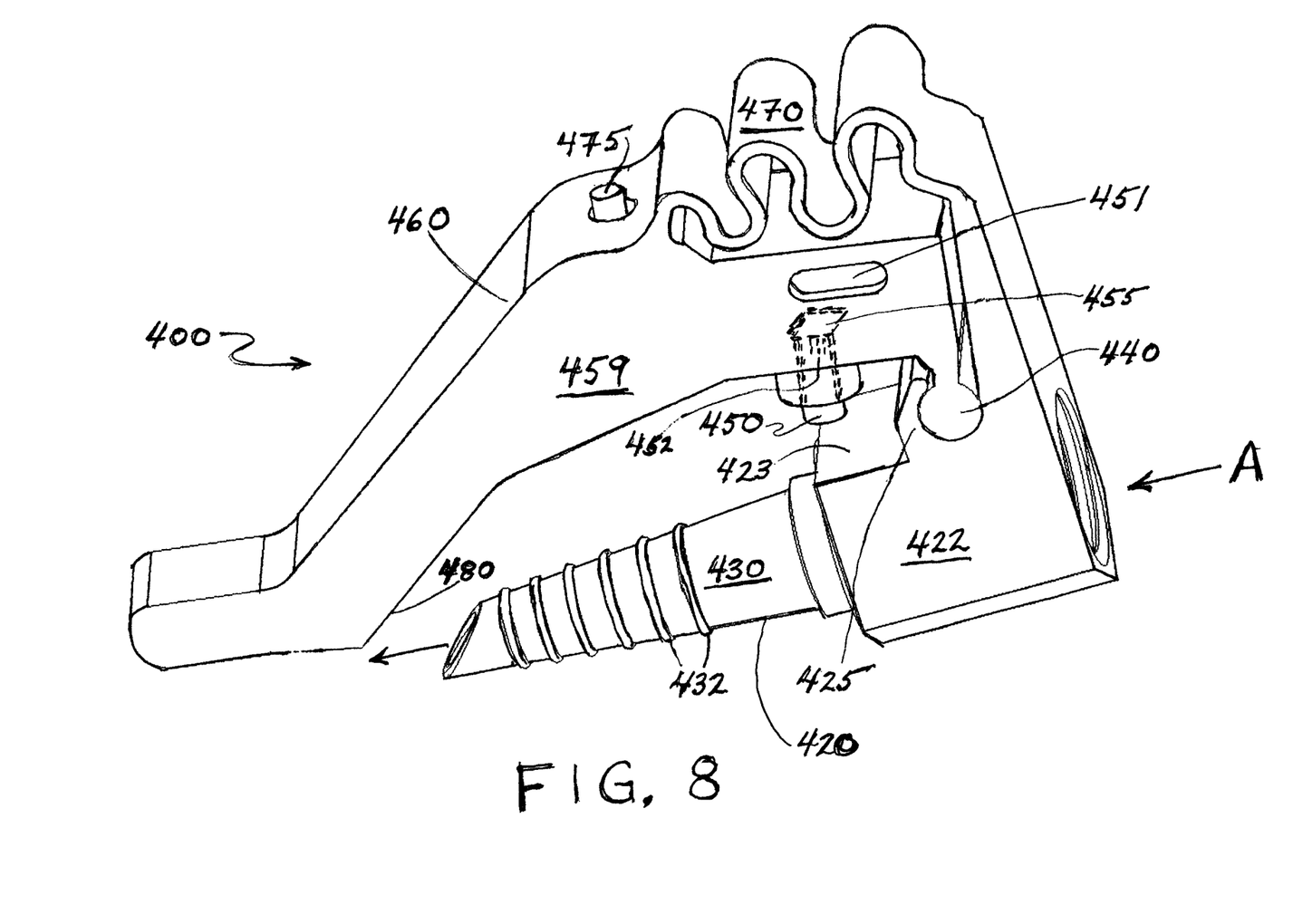
FIG. 8 is a perspective view of another embodiment that includes a microswitch and an alarm circuit chip.

FIG. 8 depicts yet another embodiment of the present invention. Here the invention 400 is comprised generally of fixed arm 420 and swing arm 459. It should be understood that, while the figure depicts the swing arm above the fixed arm, the invention is not so limited, and may be oriented in any direction. Fixed arm 420 includes nut adapter 422 and barbed nipple 430 with barbs 432. At the bottom portion of nut adapter 422 is latch 425. Gas flows through the interior of fixed arm 420 in the direction indicated by arrow A. Swing arm 459 has a base 460 and spring 470. Latch 425, hinge 440, and spring 470 urge swing arm 459 to rotate around hinge 440 toward fixed arm 420 in a manner similar to that described for the embodiment depicted in FIGS. 1-3.

As with the embodiment of FIGS. 1-3, when a tube (not shown in FIG. 8) is on barbed nipple 430, it prevents fixed arm 420 and swing arm 459 from completely moving or rotating toward each other. If the tube comes off barbed nipple 430, spring 470 causes swing arm 459 to rotate further toward fixed arm 420. The rotation is sufficient to bring button 450 into contact with the bottom 423 of nut adapter 422. Button 450 is part of a microswitch that includes electrical contacts 452 located inside swing arm 459. When button 450 is depressed slightly, it makes connection with electrical contacts 452. This causes an electrical current to flow in circuit board 455, located in electrical compartment 451 with sound port 453, all of which are in swing arm 459. The current actuates an audible alarm (not shown) located on circuit board 455. In the preferred embodiment, circuit board 455 contains a microprocessor that can be programmed to control a variety of parameters. These can include the delay (if any) in sounding the alarm after the tube has been disconnected, the duration of the alarm, and the timing cycle (if any) during which the alarm can be intermittently turned on and off. Circuit board 455 also contains, or is connected to, a small battery (not shown) to power the alert mechanism. The circuit board or the microprocessor may also contain a monitoring circuit to check the battery strength, so there is no electronic failure of the device.

As depicted in FIG. 8, the sound from the alarm travels through sound port 453. Alternatively, or additionally, the sound could travel through a passageway in button 450 and into the surrounding air so that the alarm or alerting sound can be heard. As discussed earlier, the invention need not have an audible alert directly attached to swing arm 459. Circuit board 455 can generate a WIFI or BLUETOOTH® signal to a remote receiver that can be located in a patient's room or even at a nurses' station. The receiver, in turn, can relay the signal to virtually any kind of electronically controlled alert, whether it is a whistle, a siren, a flashing light, or even a spoken voice.

Manual reset button 475 permits medical personnel to shut off the alarm. Alternatively, the invention could have a remote, wireless shutoff mechanism. For patient safety reasons, some care should be exercised in designing who can reset the device and how.

It should be noted that, unlike other embodiments, swing arm 459 does not require a passageway through which escaping oxygen can flow (see, e.g., aperture 52, FIG. 1 and aperture 352 FIG. 6). The reason for this is that the present embodiment does not require flowing oxygen to actuate an audible alarm like a whistle or to actuate a signal that ultimately causes an alert to be sounded. In the FIG. 8 embodiment, when the tube does come off, ideally end 437 of barbed nipple 430 does not sit flush against surface 480.

As depicted in FIGS. 9, 10, 11, and 12, another embodiment eliminates the need for gas to flow through a passageway in the swing arm to create an alert. Here the invention, connector 500, is comprised generally of fixed arm 520 and swing arm 559. Fixed arm 520 includes threaded adapter 522 and barbed nipple 530. A swage (or swedge) adapter could also be used to connect to a gas supply, as could other types of adapters. In the interior of fixed arm 520, gas flows through passageway 522 toward barbed nipple 530. In the present invention, it is contemplated that nipple 530 is separately attachable to fixed arm 520, although it could be formed unitarily as part of the fixed arm. Semi-circular spring section 570 is connected to, and preferably a unitary part of, swing arm 559 and urges the swing arm against barbed nipple 530. In the preferred embodiment, there are semi-circular spring sections 570 on each side of the invention and they are connected by bar 572 and to the portion of swing arm 559 that contacts barbed nipple 530. Swing arm 559, including semi-circular spring sections 570, rotates around pivot 540 that is secured in pin hole 542. Semi-circular spring 570 urges swing arm 559 against barbed nipple 530. Inside fixed arm 520 is electrical compartment 551, which contains, among other things, a circuit board 555, a battery 557, a device for generating an audible alarm 595, and a switch 560. Access to electrical compartment 551 can be had by removing screws at the top of fixed arm 520 (Note: only screw holes 580, and not the screws, are shown.). Swing arm 559 includes switch actuator 558 that, when swing arm 559 is rotated toward barbed nipple 530, contacts electrical switch 560. Preferably, part or all of the invention is formed by thermoplastic, so that it can be manufactured by a 3-D printer, but the invention should not be considered to be so limited.

Figure 12:
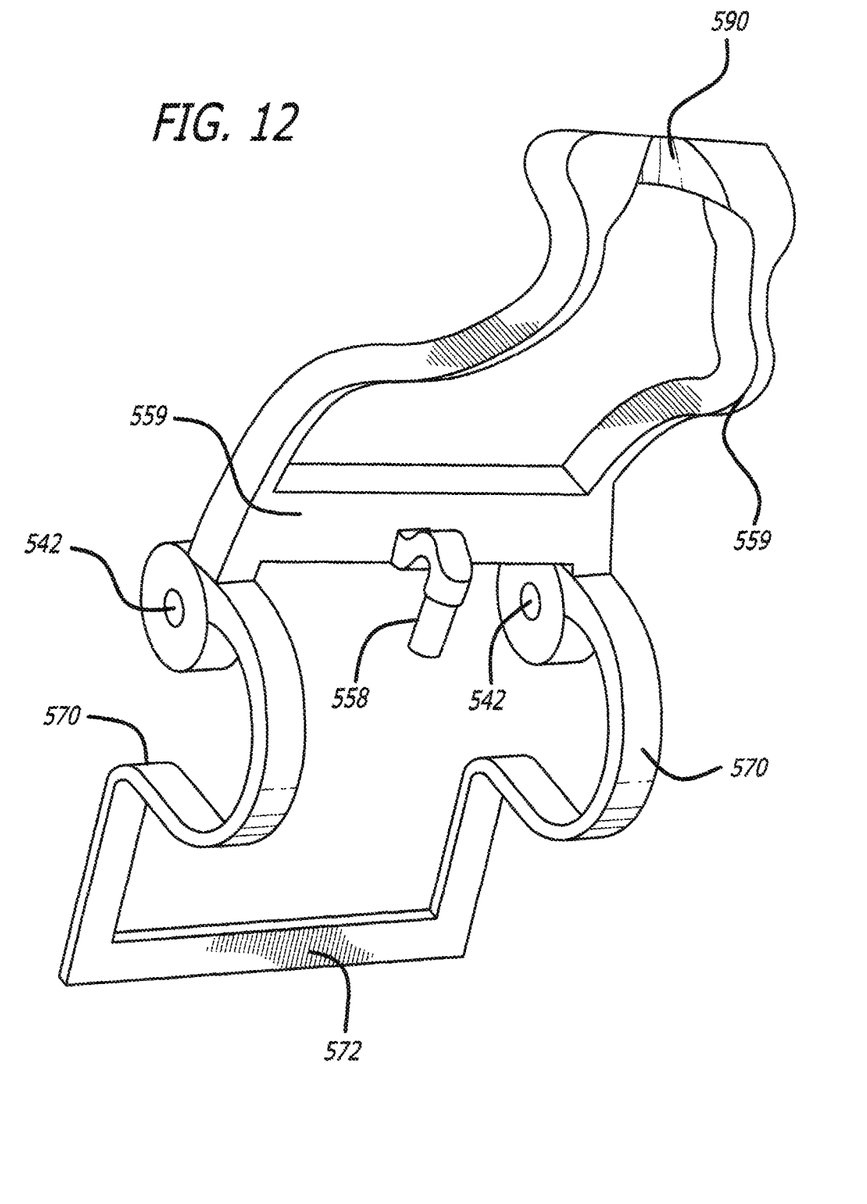
FIG. 12 is a perspective view from underneath a unitary combination of the swing arm, the switch actuator, the spring.

FIG. 12 is a perspective view of a unitary configuration of semi-circular spring 570, swing arm 559, and switch actuator 558. Notch 590 of swing arm 559 is configured to fit over the typically conical shape of barbed nipple 530. Notch 590 permits swing arm 559, and thus switch actuator 558, to rotate further when the tubing (not shown) is disconnected from barbed nipple 530. Spring 570 is not limited to the depicted semi-circular shape and could be other shapes as well.

Figure 9:
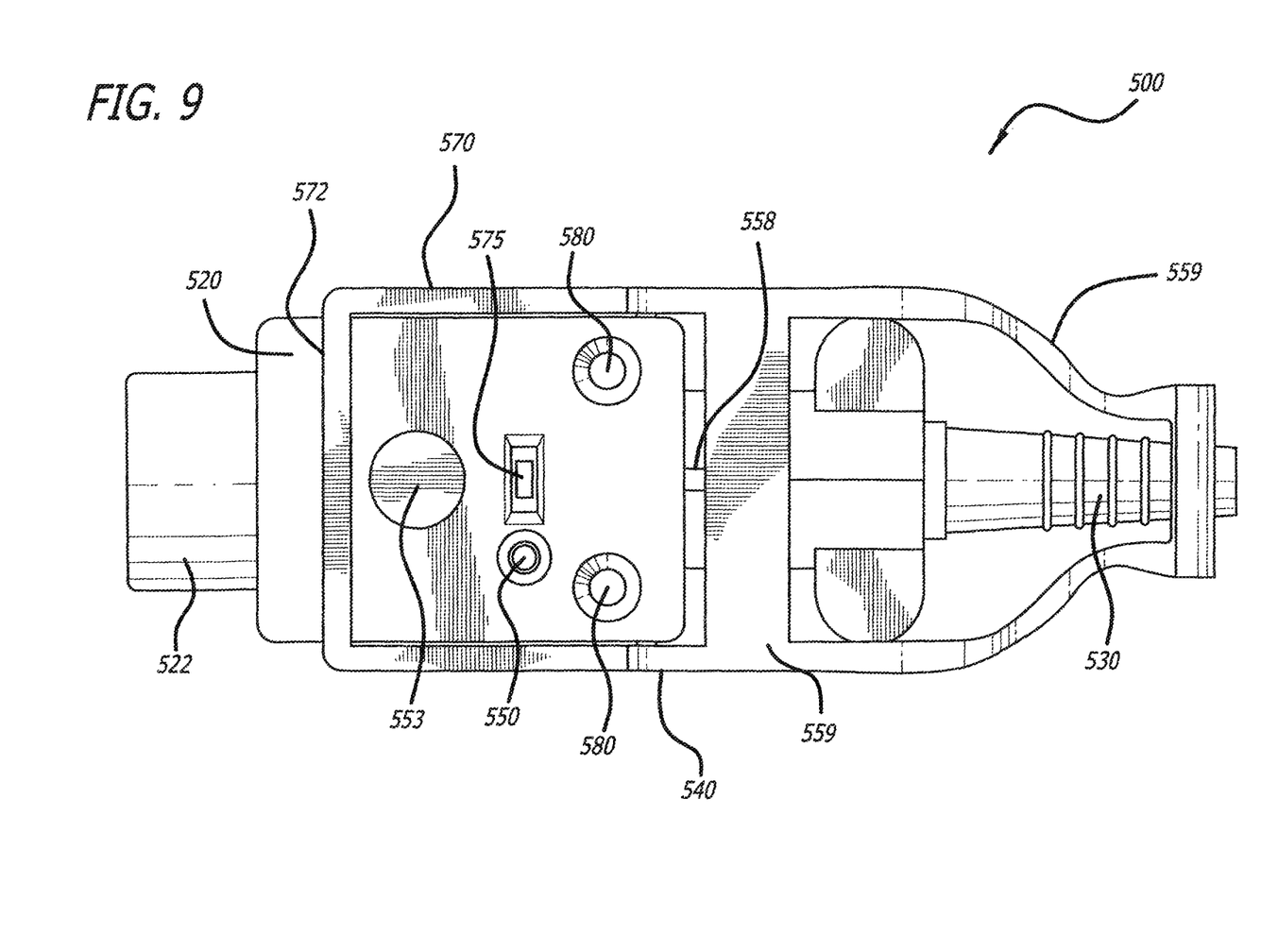
FIG. 9 is a top view of yet another embodiment that includes a microswitch and an alarm.
Figure 10:
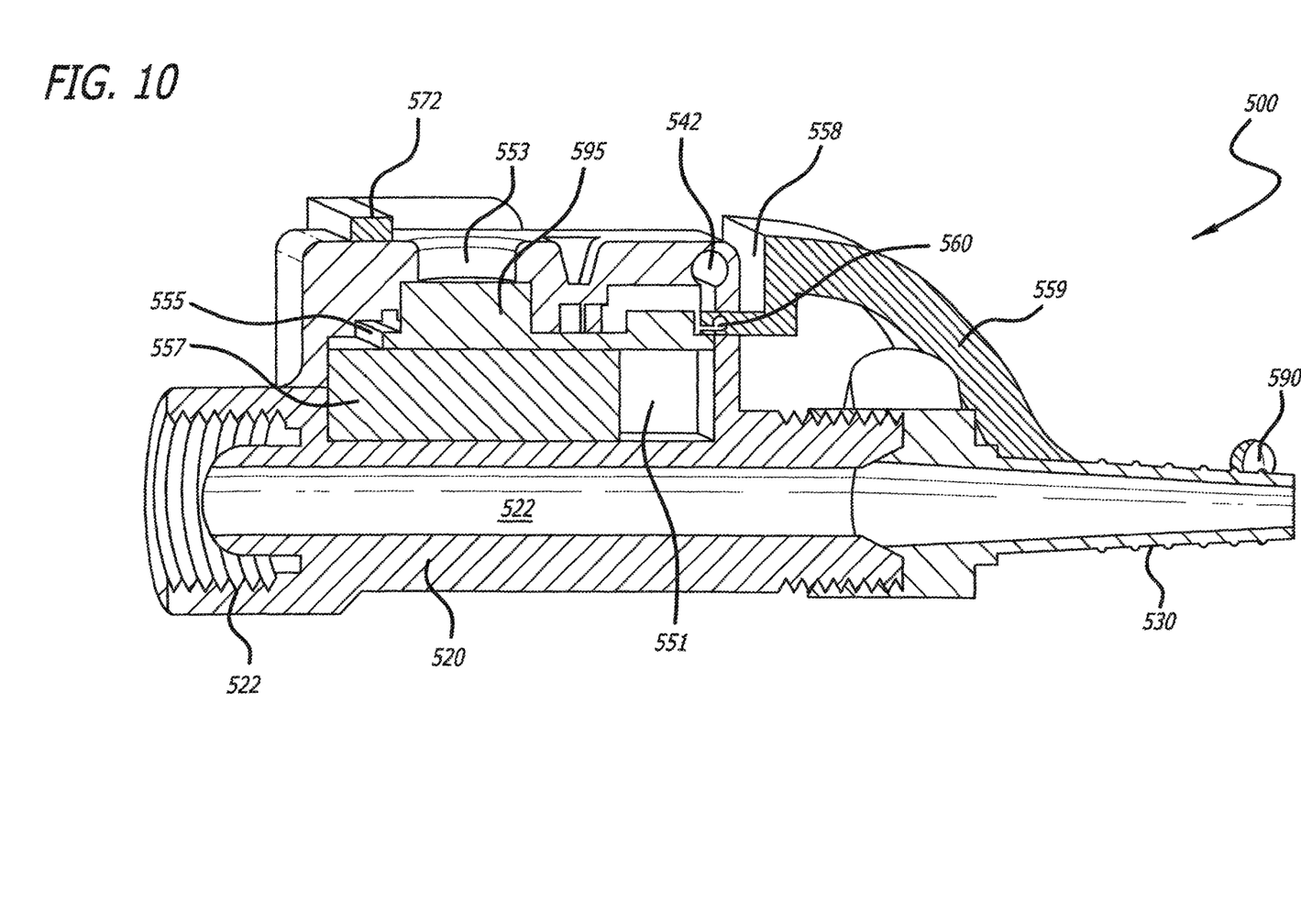
FIG. 10 is a sectional view taken longitudinally through FIG. 9.
Figure 11:
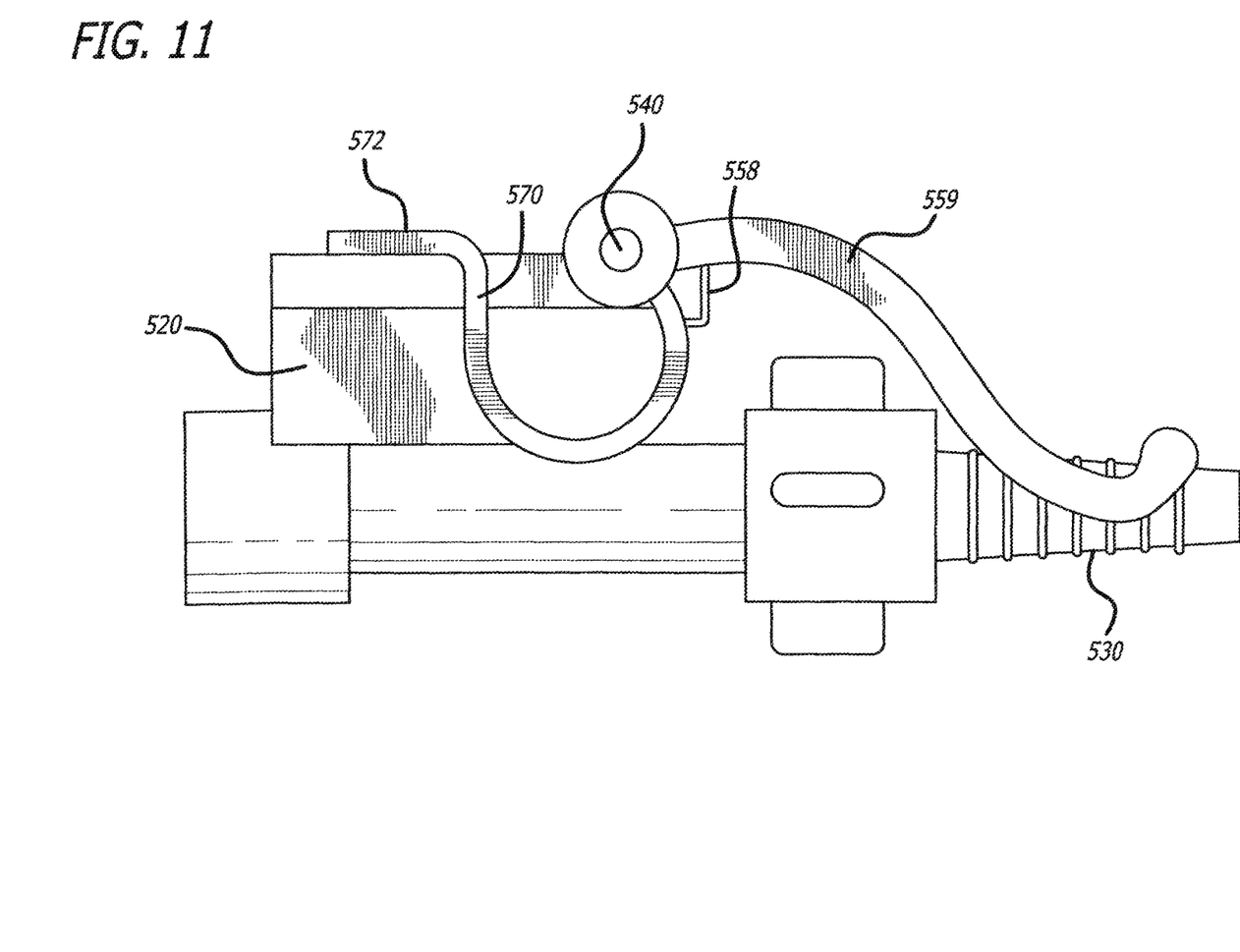
FIG. 11 is a side view of the embodiment shown in FIGS. 9 and 10.

To set up the invention, a user pulls bar 572, which causes both sides of spring 570 to pull notch 590 of swing arm 559 away from barbed nipple 530. As depicted, swing arm 559 would rotate counterclockwise. This would also disengage switch actuator 558 from switch 560 and automatically reset the alert. Then, the tube (not shown) can be slid onto barbed nipple 530. Once set, if the tube (not shown) comes off barbed nipple 530, both sections of spring 570 cause swing arm 559 to rotate toward barbed nipple 530, i.e., in a clockwise direction as shown in FIGS. 9-11. The rotation is sufficient to bring switch actuator 558 into contact with electrical switch 560. This causes an electrical current to flow in circuit board 555. The current actuates audible alarm 595 located on circuit board 555. Sound exits through sound port 553. Red LED 550 also flashes, thus providing both a visual and audible alert. Multiple mode linear switch 575 permits the user to select one of several alert modes. The preferred embodiment employs three: 1) audible, 2) visual, and 3) audible and visual. Alerts could be placed at a remote location, such as a nurses' station (not shown). Another option for the invention is for circuit board 555 to contain a microprocessor that can be programmed to control a variety of parameters, such as a delay in sounding the alarm after the tube has been disconnected, the duration of the alarm, and a timing cycle during which the alarm can be intermittently turned on and off. The circuit board may also contain a monitoring circuit to check the battery strength, so there is no electronic failure of the device.

Those of skill in the art will understand that numerous variations of the described embodiments fall within the spirit and scope of the invention, which is to be limited only by the following claims and their equivalents. For example, in the last embodiment a wired source of electrical power could be used in lieu of a battery, although the latter is preferred. Likewise, those of skill in the art understand that the present invention must seal tightly to a flow meter, regulator or wall outlet, or wherever the connection to the oxygen source is located. Precision threads, clamps, seals, and other materials may be used to insure oxygen does not leak. Those of skill in the art also recognize the interchangeability of many mechanical parts. For example, a "nut adapter" can just as easily be changed to be a bolt adapter, male threaded adapter, push-on, swedge-on, or snap-on adapter. Thus, virtually any leak-proof connection between the oxygen source and the invention would also come within the scope of the invention, even if it did not possess the interlocking threads of a nut and bolt. Spring 70 and hinge 67 can also be substituted for by a variety of equivalent springs and hinges known to those of skill in the art. As previously noted, the invention is not limited to use with oxygen. Also, while it is preferred that a nipple have barbs, if barbs are used they are not necessarily sharp in the same sense as barbed wire has sharp barbs. Those of skill in the art understand that barbs on a nipple adapter are typically a series of adjacent or spaced ridges.

Other, more significant changes can be made while still falling within the scope of the invention. For example, the embodiment depicted in FIG. 4 need not incorporate chamber 157 or ball 155. Instead, a piezoelectric sensor could be placed inside flow path 135 of nipple 130, so that without chamber 157 nipple 130 would retain a generally conical frustum shape. The sensor can be pre-programmed to determine the change in oxygen pressure and velocity in flow path 135. If a tube were to become disconnected from the end of barbed nipple 130, the sensor would signal an alert mechanism such as a whistle, horn, or light source (e.g., LED) to alert personnel that the oxygen tube has been disconnected. With a piezoelectric sensor the alerting mechanism need not be part of barbed nipple 130, although it can be. The designer may elect to make the alerting mechanism electrical, mechanical, or electromechanical. Likewise, whistle 50 as depicted in FIGS. 1-3 could be replaced by a variety of alerting mechanisms, such as a piezoelectric sensor associated with a horn or light connected to but not part of base 60. Moreover, such connection could be hardwired or wireless.

Accordingly, the scope of the present invention is intended to embrace all such modifications, variations, and alternatives that fall within the scope of the following claims, together with all equivalents thereof.

What is claimed is:

1. A connector for signaling that a tube has become disconnected from the connector, comprising:
    a fixed arm including a gas passageway;
    a first adapter configured for connection to a source of gas;
    a second adapter connectable to a nipple;
    a swing arm, including a switch actuator;
    a spring urging the swing arm toward the nipple;
    a pivot joining the fixed arm and the swing arm;
    a switch disposed on the fixed arm and actuatable by movement of the switch actuator when the tube is disconnected from the nipple; and
    an electrical signal generator, responsive to the switch, to actuate an alert that the tube has become disconnected.

2. The connector of claim 1, wherein the alert is on the connector.

3. The connector of claim 1, wherein the alert is an audible sound that passes through a sound port.

4. The connector of claim 3, wherein the sound source is disposed in the fixed arm.

5. The connector of claim 1, wherein the alert is a light.

6. The connector of claim 1, wherein the alert is a light or an audible sound.

7. The connector of claim 1, wherein the connector is thermoplastic.

8. The connector of claim 1, wherein the first adapter is joined to the gas source by one of a threaded or a swage connection.

9. The connector of claim 1, wherein the electrical signal generator and alert include an electrical power source, and the alert is responsive to a signal transmitted through the switch.

10. The connector of claim 1, wherein the connector includes a plurality of selectable alerts.

11. A connector for signaling that tubing has become disconnected from the connector, comprising:
    a fixed arm, a nipple connected to the fixed arm, an adapter for connecting the fixed arm to a source of gas, and an electrical compartment;
    a swing arm, movably connected to the fixed arm, that includes a spring that urges the swing arm to move toward the fixed arm when tubing becomes disconnected;
    a switch disposed in the electrical compartment and actuatable when the swing arm rotates toward the fixed arm when the tubing is disconnected;
    an electronic signal generator disposed in the electrical compartment and responsive to the switch being activated; and,
    an alert disposed on the fixed arm and responsive to a signal from the electronic signal generator.

12. The connector of claim 11, wherein the swing arm includes a switch actuator that moves with the swing arm.

13. The connector of claim 11, wherein the alert comprises a sound source located in the electrical compartment and responsive to the signal generator.

14. The connector of claim 11, wherein the alert is a light source.

15. The connector of claim 11, further including a second switch for selecting the type of alert.

16. The connector of claim 15, wherein the second switch is capable of selecting a plurality of simultaneous alerts.

17. The connector of claim 11, wherein the alert is remote from the connector.

18. The connector of claim 11, wherein the electronic signal generator and the alert are powered by a battery disposed in the electrical compartment.

* * * * *